(12) United States Patent
Sun et al.

(10) Patent No.: US 12,071,435 B2
(45) Date of Patent: Aug. 27, 2024

(54) TLR8 AGONIST

(71) Applicant: CHIA TAI TIANQING PHARMACEUTICAL GROUP CO., LTD., Jiangsu (CN)

(72) Inventors: Fei Sun, Shanghai (CN); Zhe Cai, Shanghai (CN); Charles Z. Ding, Shanghai (CN); Shuhui Chen, Shanghai (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 688 days.

(21) Appl. No.: 17/286,316

(22) PCT Filed: Oct. 18, 2019

(86) PCT No.: PCT/CN2019/111897
§ 371 (c)(1),
(2) Date: Apr. 16, 2021

(87) PCT Pub. No.: WO2020/078455
PCT Pub. Date: Apr. 23, 2020

(65) Prior Publication Data
US 2021/0340141 A1 Nov. 4, 2021

(30) Foreign Application Priority Data

Oct. 19, 2018 (CN) .......................... 201811221301.1
Mar. 4, 2019 (CN) .......................... 201910161144.8

(51) Int. Cl.
*C07D 471/04* (2006.01)
*C07D 403/12* (2006.01)

(52) U.S. Cl.
CPC .......... *C07D 471/04* (2013.01); *C07D 403/12* (2013.01)

(58) Field of Classification Search
CPC ........................... C07D 403/12; C07D 471/04
See application file for complete search history.

(56) References Cited

U.S. PATENT DOCUMENTS 9,663,474 B2  5/2017  Last et al.

FOREIGN PATENT DOCUMENTS

| WO | 2014/076221 A1 | 5/2014 | |
|----|----|----|----|
| WO | 2016/141092 A1 | 9/2016 | |
| WO | WO-2016141092 A1 * | 9/2016 | ........... A61K 31/517 |
| WO | 2018/045144 A1 | 3/2018 | |
| WO | WO 2018/107200 A1 | 6/2018 | |

OTHER PUBLICATIONS

Yu (Bioorganic and Medicinal Chemistry Letters vol. 2 pp. 1121-1126 published 1992) (Year: 1992).*
Solomon et al., "Design, synthesis fo 4-aminoquinoline-derived thiazolidines and their antimalarial activity and heme polymerization inhibition studies," J. of Enzyme Inhibitions and Medicinal Chem, vol. 28, No. 3, pp. 619-626 (iDec. 31, 2013).

* cited by examiner

*Primary Examiner* — Clinton A Brooks
*Assistant Examiner* — George W Kosturko
(74) *Attorney, Agent, or Firm* — Oliff PLC

(57) ABSTRACT

The present invention relates to a structurally novel TLR8 (Toll-like receptor 8) agonist and, in particular, to a compound thereof of formula (I), a pharmaceutically acceptable salt and an isomer thereof.

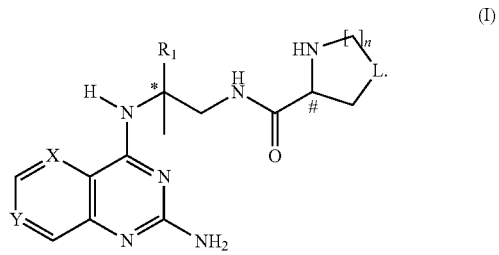

14 Claims, No Drawings

TLR8 AGONIST

The present application claims the following priority:

Chinese Patent Application CN201811221301.1, filed on Oct. 19, 2018;

Chinese Patent Application CN201910161144.8, filed on Mar. 4, 2019.

TECHNICAL FIELD

The present application relates to a structurally novel TLR8 (Toll-like receptor 8) agonist, and in particular to a compound of formula (I), an isomer thereof or a pharmaceutically acceptable salt thereof, and use of the compound of formula (I) or the pharmaceutically acceptable salt thereof in treating diseases related to virus infection.

BACKGROUND

Toll-like receptors (TLRs) are an important class of protein molecules involved in non-specific immunity (innate immunity), and are also a bridge linking non-specific immunity and specific immunity. TLRs are single transmembrane non-catalytic proteins that are expressed primarily in a range of immune cells such as dendritic cells, macrophages, monocytes, T cells, B cells, and NK cells. TLRs are capable of recognizing molecules with conserved structures derived from microorganisms. They can recognize the microorganisms and activate the body to generate immune cell responses when microorganisms break through the physical barriers of the body, such as skin and mucosa. For example, TLR1, TLR2, TLR4, TLR5 and TLR6 mainly recognize extracellular stimuli such as lipopolysaccharide, lipopeptide, and flagellin of bacteria, while TLR3, TLR7, TLR8 and TLR9 function in cell endosomes, such as binding to their ligands after phagocytosis and dissolution of the envelope and recognizing nucleic acids of microorganisms.

Among the different subtypes of TLR, TLR8 has unique functions: TLR8 is expressed primarily in monocytes, macrophages, and myeloid dendritic cells. The signaling pathway of TLR8 can be activated by bacterial single-stranded RNAs, small molecule agonists, and microRNAs. Activation of TLR8 results in the production of Th1 polar cytokines such as IL-12, IL-18, TNF-α and IFN-γ, and various co-stimulatory factors such as CD80 and CD86. These cytokines can activate and amplify innate and adaptive immune responses and provide a beneficial treatment regimen for diseases involving anti-virus, anti-infection, autoimmunity, tumors, and the like. For example, with respect to hepatitis B, activation of TLR8 on antigen presenting cells and other immune cells in the liver can activate cytokines such as IL-12, which in turn activates specific T cells and NK cells that are depleted by the virus, thereby reconstituting the antiviral immunity in the liver.

The selective TLR8 agonist VTX-2337 from VentiRX Pharmaceuticals is first used clinically for the evaluation of different tumors, and the mode of administration of VTX-2337 is subcutaneous injection. Gilead Sciences reported an oral TLR8 agonist GS-9688 for the treatment of chronic hepatitis B infection, which is currently in clinical phase II. However, its structure has not disclosed yet.

VTX-2337

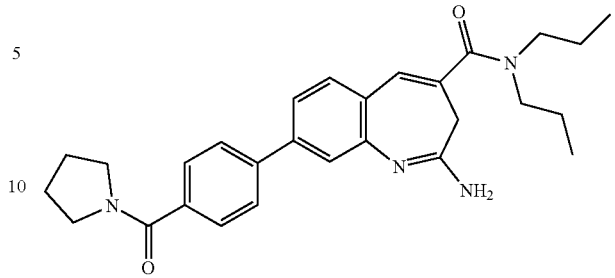

SUMMARY OF THE INVENTION

The present application provides a compound of formula (I), an isomer thereof and a pharmaceutically acceptable salt thereof, (I)

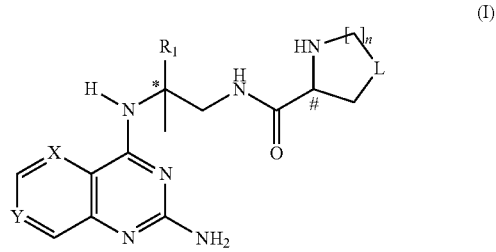

wherein, the carbon atom with "*" is a chiral carbon atom present in a form of a single (R) or (S) enantiomer or in a form enriched with one enantiomer;

the carbon atom with "#" is a chiral carbon atom present in a form of a single (S) enantiomer or in a form enriched with (S) enantiomer;

X is selected from the group consisting of CH and N;

Y is selected from the group consisting of $CR_2$ and N;

n is selected from the group consisting of 0, 1, 2 and 3;

L is selected from the group consisting of —O— and —$CR_3R_4$—;

$R_1$ is selected from the group consisting of $C_{1-6}$ alkyl, wherein the $C_{1-6}$ alkyl is optionally substituted with 1, 2 or 3 $R_a$;

$R_2$ is selected from the group consisting of H, CN, $NH_2$, halogen, $C_{1-6}$ alkyl, $C_{1-6}$ alkyl-O—, $NHR_b$, $N(R_c)_2$, $C_{3-6}$ cycloalkyl, —C(=O)$R_d$, —C(=O)—O—$R_e$, —O—C(=O)—$R_e$, —S(=O)$_2R_f$ and —S(=O)$R_g$;

$R_3$ and $R_4$ are each independently selected from the group consisting of H, halogen and $C_{1-3}$ alkyl, wherein the $C_{1-3}$ alkyl is optionally substituted with 1, 2 or 3 $R_h$;

alternatively, $R_3$ and $R_4$ are linked to form a 3-6 membered saturated ring, wherein the 3-6 membered saturated ring is optionally substituted with 1, 2 or 3 $R_i$;

$R_a$, $R_b$, $R_c$, $R_d$, $R_e$, $R_f$, $R_g$, $R_h$ and $R_i$ are each independently selected from the group consisting of F, Cl, Br, I, OH, CN, $NH_2$, $C_{1-6}$ alkyl, $C_{1-6}$ heteroalkyl, $C_{3-6}$ cycloalkyl, 3-6 membered heterocycloalkyl, phenyl and 5-6 membered heteroaryl, wherein the $C_{1-6}$ alkyl, $C_{1-6}$ heteroalkyl, $C_{3-6}$ cycloalkyl, 3-6 membered heterocycloalkyl, phenyl and 5-6 membered heteroaryl are optionally substituted with 1, 2 or 3 R;

R is each independently selected from the group consisting of F, Cl, Br, I, OH, CN, NH$_2$, CH$_3$,

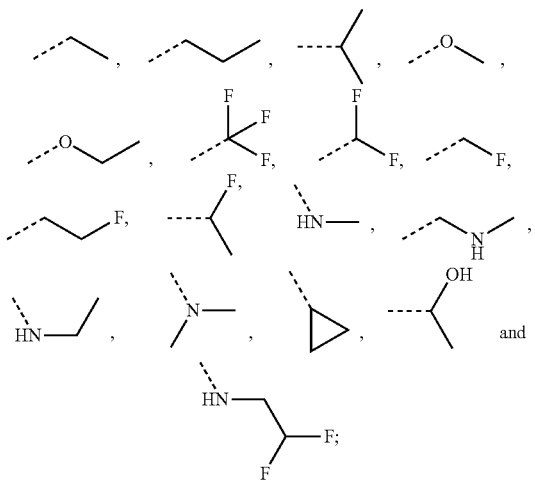

and the C$_{1-6}$ heteroalkyl, 3-6 membered heterocycloalkyl and 5-6 membered heteroaryl each contain 1, 2, 3 or 4 heteroatoms or heteroatom groups independently selected from the group consisting of —NH—, —O—, —S— and N.

In some embodiments of the present application, R$_a$, R$_b$, R$_c$, R$_d$, R$_e$, R$_f$, R$_g$, R$_h$ and R$_i$ are each independently selected from the group consisting of F, Cl, Br, I, OH, CN, NH$_2$, CH$_3$,

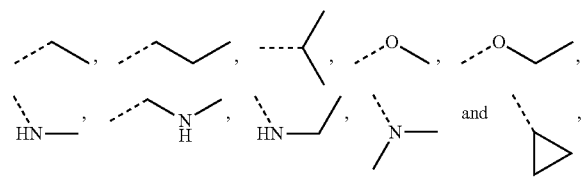

wherein the CH$_3$,

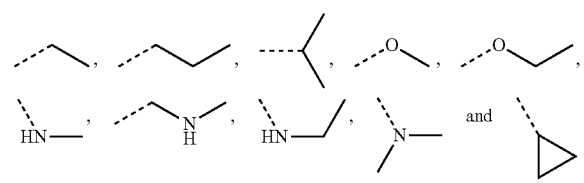

are optionally substituted with 1, 2 or 3 R.

In some embodiments of the present application, R$_a$, R$_b$, R$_c$, R$_d$, R$_e$, R$_f$, R$_g$, R$_h$ and R$_i$ are each independently selected from the group consisting of F, Cl, Br, I, OH, CN, NH$_2$, CH$_3$,

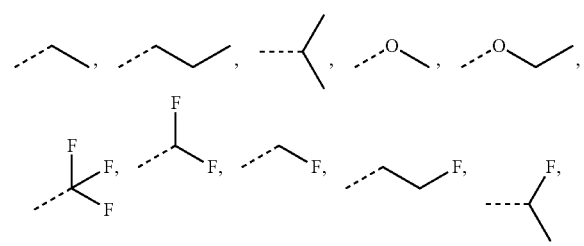

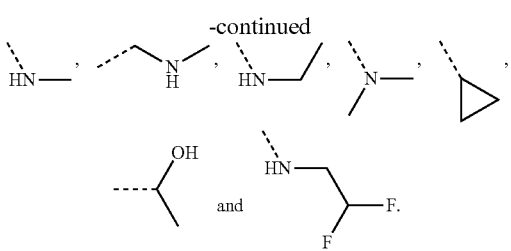

In some embodiments of the present application, R$_1$ is selected from the group consisting of

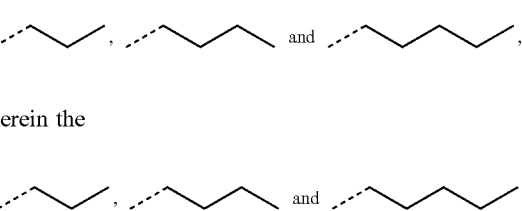

wherein the

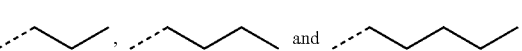

are optionally substituted with 1, 2 or 3 R$_a$.

In some embodiments of the present application, R$_1$ is selected from

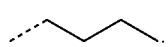.

In some embodiments of the present application, R$_2$ is selected from the group consisting of H, CN, F, Cl, Br, I, CH$_3$,

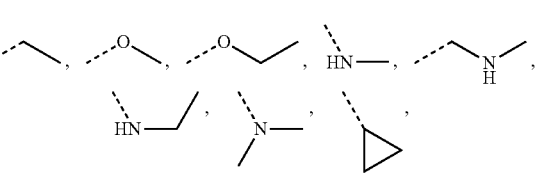

—C(=O)CH$_3$, —C(=O)—O—CH$_3$, —O—C(=O)—CH$_3$, —S(=O)$_2$CH$_3$ and —S(=O)CH$_3$.

In some embodiments of the present application, R$_2$ is selected from the group consisting of H and F.

In some embodiments of the present application, R$_3$ and R$_4$ are each independently selected from the group consisting of H, F, Cl, Br and CH$_3$, wherein the CH$_3$ is optionally substituted with 1, 2 or 3 R$_h$.

In some embodiments of the present application, R$_3$ and R$_4$ are each independently selected from the group consisting of H and F.

In some embodiments of the present application, the structural unit

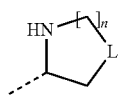

is selected from the group consisting of

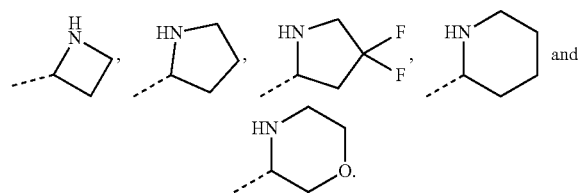

In some embodiments of the present application, $R_a$, $R_b$, $R_c$, $R_d$, $R_e$, $R_f$, $R_g$, $R_h$ and $R_i$ are each independently selected from the group consisting of F, Cl, Br, I, OH, CN, $NH_2$, $CH_3$,

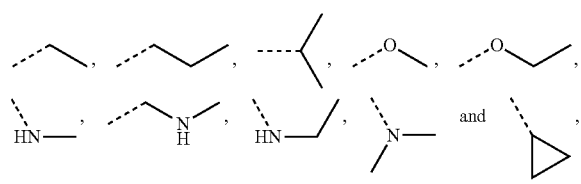

wherein the $CH_3$,

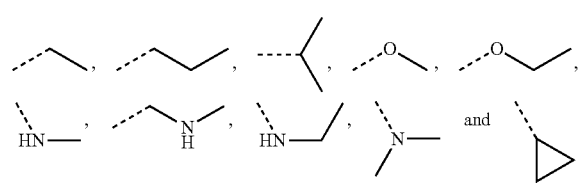

are optionally substituted with 1, 2 or 3 R, while other variables are defined as herein.

In some embodiments of the present application, $R_a$, $R_b$, $R_c$, $R_d$, $R_e$, $R_f$, $R_g$, $R_h$ and $R_i$ are each independently selected from the group consisting of F, Cl, Br, I, OH, CN, $NH_2$, $CH_3$,

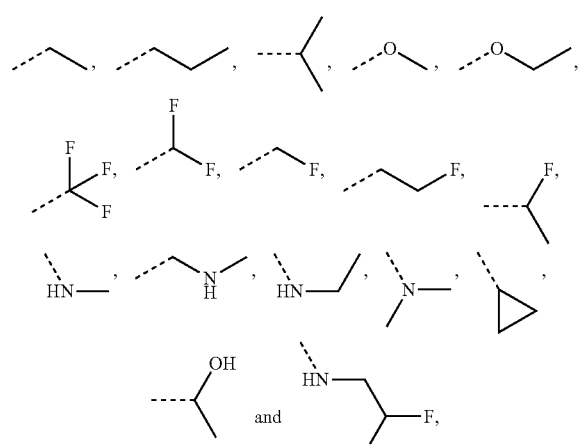

while other variables are defined as herein.

In some embodiments of the present application, $R_1$ is selected from the group consisting of

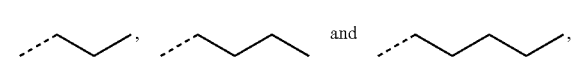

wherein the

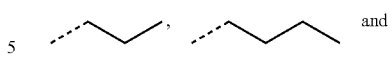

are optionally substituted with 1, 2 or 3 $R_a$, while other variables are defined as herein.

In some embodiments of the present application, $R_1$ is selected from

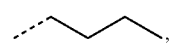

while other variables are defined as herein.

In some embodiments of the present application, $R_2$ is selected from the group consisting of H, CN, F, Cl, Br, I, $CH_3$,

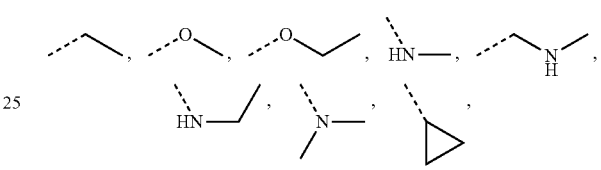

—C(=O)$CH_3$, —C(=O)—O—$CH_3$, —O—C(=O)—$CH_3$, —S(=O)$_2$$CH_3$ and —S(=O)$CH_3$, while other variables are defined as herein.

In some embodiments of the present application, $R_2$ is selected from the group consisting of H and F, while other variables are defined as herein.

In some embodiments of the present application, $R_3$ and $R_4$ are each independently selected from the group consisting of H, F, Cl, Br and $CH_3$, wherein the $CH_3$ is optionally substituted with 1, 2 or 3 $R_h$, while other variables are defined as herein.

In some embodiments of the present application, $R_3$ and $R_4$ are each independently selected from the group consisting of H and F, while other variables are defined as herein.

In some embodiments of the present application, the structural unit

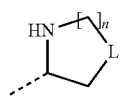

is selected from the group consisting of

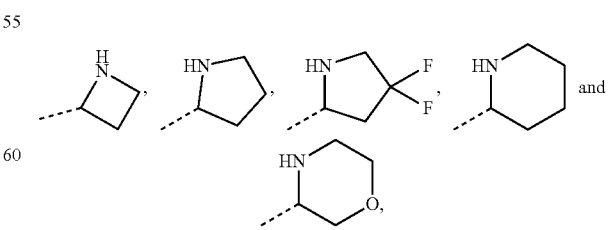

while other variables are defined as herein.

In some embodiments of the present application, provided are the compound above, an isomer thereof and a pharmaceutically acceptable salt thereof, wherein the compound is selected from compounds represented by the formula below

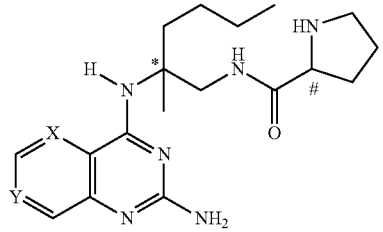

(I-1)

wherein,

"*", "a", X and Y are defined as above.

The present application also provides a compound of a formula selected from the group consisting of the formulas below, an isomer thereof and a pharmaceutically acceptable salt thereof:

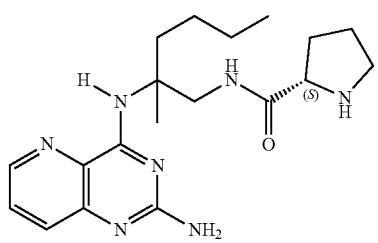

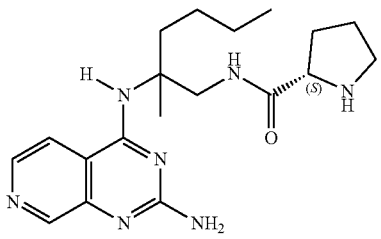

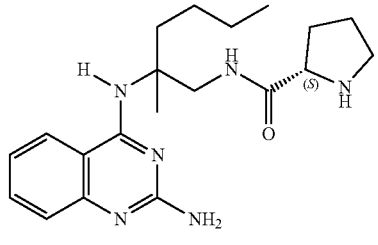

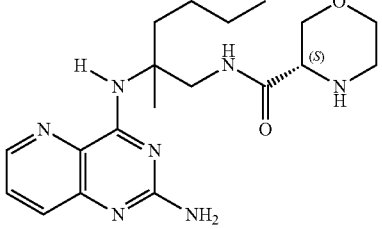

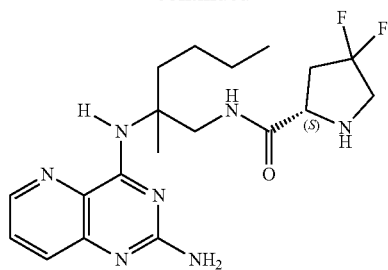

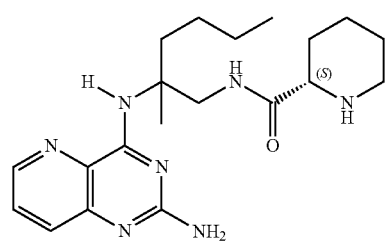

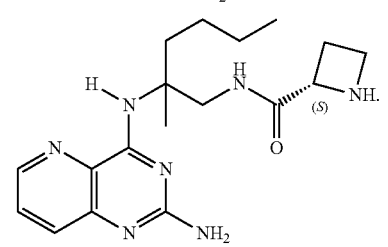

The present application also provides a compound of a formula selected from the group consisting of the formulas below, an isomer thereof and a pharmaceutically acceptable salt thereof:

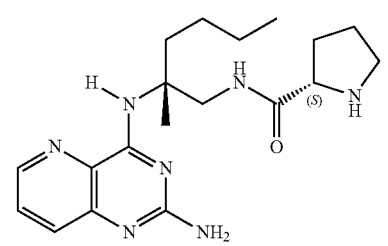

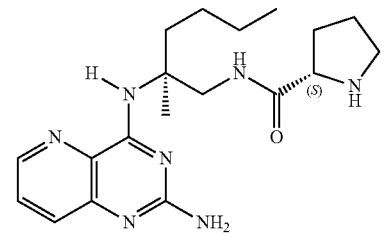

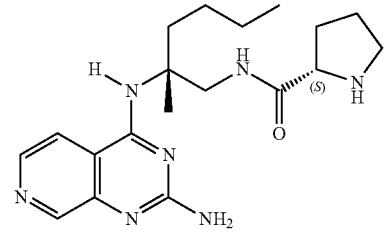

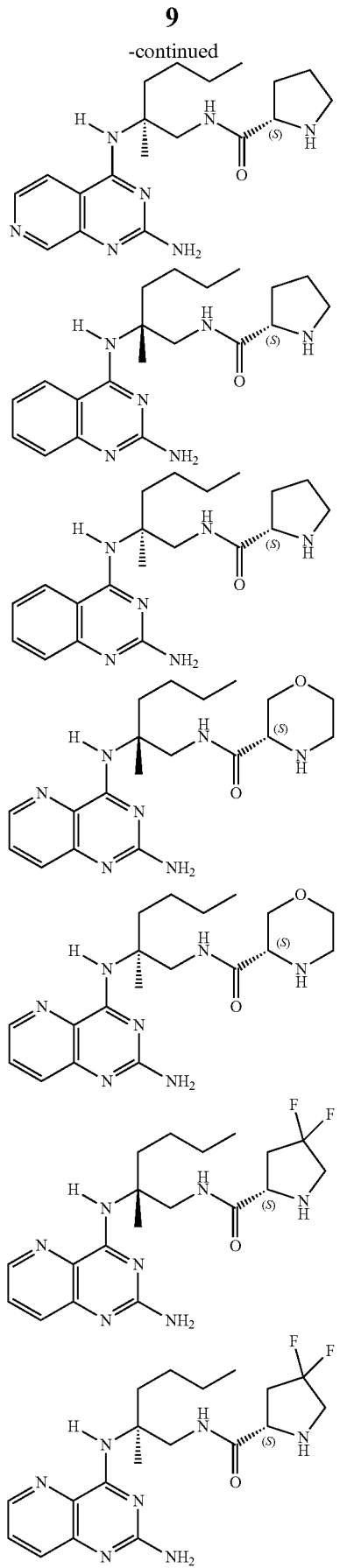

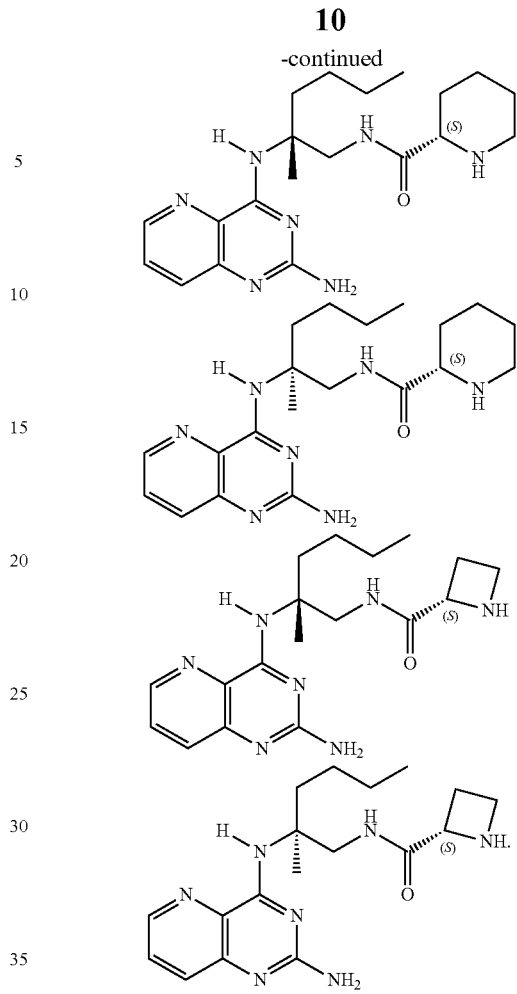

The present application also provides use of the compound, the isomer thereof and the pharmaceutically acceptable salt thereof in preparing a medicament for treating hepatitis B virus.

Some other embodiments of the present application can be obtained by the arbitrary combination of the above variables.

Technical Effects

The compound of the present application has good TLR8 agonistic activity and specific selectivity, and exhibits desirable activity for inducing TLR8 pathway specific cytokines (IL-12p40, IFN-γ).

Definitions and Description

Unless otherwise stated, the following terms and phrases used herein are intended to have the following meanings. A particular term or phrase, unless otherwise specifically defined, should not be considered as uncertain or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound disclosed herein, which is prepared from the compound having particular substituents disclosed herein and a relatively nontoxic acid or base. When the compound of the present application contains a relatively acidic functional group, a base addition salt can be given by contacting the neutral form of such a compound with a sufficient amount of a base in a pure solution or a suitable inert solvent. Pharmaceutically acceptable base addition salts include sodium, potassium, calcium, ammonium, organic amine, or magnesium salts, or similar salts. When the compound of the present application contains a relatively basic functional group, an acid addition salt can be given by contacting the neutral form of such a compound with a sufficient amount of an acid in a pure solution or a suitable inert solvent. Examples of pharmaceutically acceptable acid addition salts include salts derived from inorganic acids, such as hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid; and salts derived from organic acids, such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid and methanesulfonic acid. Also included are salts of amino acids (such as arginine) and salts of organic acids such as glucuronic acid. Certain specific compounds disclosed herein contain both basic and acidic functional groups that allow the compounds to be converted into either base or acid addition salts.

The pharmaceutically acceptable salts of the present application can be synthesized from a parent compound having an acidic or basic group by conventional chemical methods. In general, such salts are prepared by the following method: the free acid or base form of the compound reacting with a stoichiometric amount of the appropriate base or acid in water or an organic solvent or a mixture thereof.

The compound of the present application may have a specific geometric or stereoisomeric form. All such compounds are contemplated herein, including cis and trans isomers, (−)- and (+)-enantiomers, (R)- and (S)-enantiomers, diastereoisomers, (D)-isomers, (L)-isomers, and racemic mixtures and other mixtures thereof, such as an enantiomer or diastereoisomer enriched mixture, all of which are encompassed within the scope of the present application. Substituents such as alkyl may have an additional asymmetric carbon atom. All these isomers and mixtures thereof are encompassed within the scope of the present application.

Unless otherwise stated, the term "enantiomer" or "optical isomer" refers to stereoisomers that are mirror images of each other.

Unless otherwise stated, the term "cis-trans isomer" or "geometric isomer" results from the inability of a single bond of a ring carbon atom or a double bond to rotate freely.

Unless otherwise stated, the term "diastereoisomer" refers to stereoisomers in which molecules each have two or more chiral centers and are not mirror images of each other.

Unless otherwise stated, "(+)" stands for dextrorotation, "(−)" stands for levorotation, and "(±)" stands for racemization.

Unless otherwise stated, the absolute configuration of a stereogenic center is represented by a wedged solid bond ( ) and a wedged dashed bond ( ) and the relative configuration of a stereogenic center is represented by a straight solid bond ( ) and a straight dashed bond ( ). A wavy line ( ) represents a wedged solid bond ( ) or a wedged dashed bond ( ), or a wavy line ( ) represents a straight solid bond ( ) or a straight dashed bond ( ).

Unless otherwise stated, the term "enriched with one isomer", "isomer enriched", "enriched with one enantiomer", or "enantiomer enriched" means that the content of one of the isomers or enantiomers is less than 100% and more than or equal to 60%, 70%, 80%, 90%, 95%, 96%, 97%, 98%, 99%, 99.5%, 99.6%, 99.7%, 99.8%, or 99.9%.

Unless otherwise stated, the term "isomeric excess" or "enantiomeric excess" refers to the difference between the relative percentages of two isomers or enantiomers. For example, if the content of one isomer or enantiomer is 90% and the content of the other isomer or enantiomer is 10%, the isomeric or enantiomeric excess (ee value) is 80%.

Optically active (R)- and (S)-isomers and D and L isomers can be prepared by chiral synthesis or chiral reagents or other conventional techniques. If one kind of enantiomer of certain compound disclosed herein is to be obtained, the desired pure enantiomer can be prepared by asymmetric synthesis or derivatization using a chiral auxiliary, wherein the resulting diastereoisomeric mixture is separated and the auxiliary group is cleaved. Alternatively, when the molecule contains a basic functional group (such as amino) or an acidic functional group (such as carboxyl), the compound reacts with an appropriate optically active acid or base to form a salt of the diastereoisomer, which is then subjected to diastereoisomeric resolution through conventional methods in the art to get the pure enantiomer. Furthermore, the enantiomer and the diastereoisomer are generally isolated through chromatography using a chiral stationary phase, optionally in combination with chemical derivatization (e.g., carbamate generated from amines). The compound of the present application may contain an unnatural proportion of atomic isotope at one or more of the atoms that constitute the compound. For example, the compound may be labeled with a radioisotope, such as tritium ($^3$H), iodine-125 ($^{125}$I), or C-14 ($^{14}$C). For another example, hydrogen can be substituted by deuterium to form a deuterated drug, and the bond formed by deuterium and carbon is firmer than that formed by common hydrogen and carbon. Compared with an un-deuterated drug, the deuterated drug has the advantages of reduced toxic side effect, increased stability, enhanced efficacy, prolonged biological half-life and the like. All isotopic variations of the compound of the present application, whether radioactive or not, are encompassed within the scope of the present application. "Optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted by substituent(s) which may include deuterium and hydrogen variants, as long as the valence of the specific atom is normal and the substituted compound is stable. When the substituent is an oxygen (i.e., =O), it means that two hydrogen atoms are substituted. Substitution by oxygen does not occur on aromatic groups. The term "optionally substituted" means that an atom can be substituted by a substituent or not. Unless otherwise specified, the type and number of the substituent may be arbitrary as long as being chemically achievable.

When any variable (e.g., R) occurs more than once in the constitution or structure of a compound, the definition of the variable in each case is independent. Thus, for example, if a group is substituted by 0-2 R, the group can be optionally substituted by two R at most, and the definition of R in each case is independent. Furthermore, a combination of a substituent and/or a variant thereof is permissible only if the combination can result in a stable compound.

When the number of a linking group is 0, for example, —(CRR)$_0$—, it means that the linking group is a single bond.

When one of variants is selected from single bond, then two groups bonding by this variant are bonded directly. For example, in A-L-Z, when L represents a single bond, it means that the structure is actually A-Z.

When a substituent is absent, it means that the substituent does not exist. For example, when X in A-X is absent, the structure is actually A. When a substituent is listed without indicating the atom via which such substituent is bonded to the group to be substituted, then such substituent may be bonded via any atom in such substituent. For example, pyridinyl as a substituent can be linked to the group to be substituted through any carbon atom on the pyridine ring.

When the enumerative linking group does not indicate the direction for linking, the direction for linking is arbitrary. For example, when the linking group L contained in

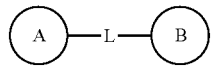

is -M-W—, -M-W— can either link ring A and ring B in a direction same as left-to-right reading order to form

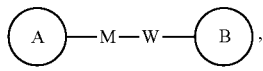

or link ring A and ring B in an opposing direction to form

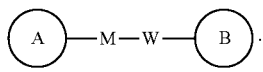

A combination of the linking group, a substituent and/or a variant thereof is permissible only if the combination can result in a stable compound.

Unless otherwise specified, the number of atoms on a ring is generally defined as the member number of the ring. For example, "5-7 membered ring" refers to a "ring" on which 5 to 7 atoms are arranged in a circle.

Unless otherwise specified, "3-6 membered saturated ring" refers to cycloalkyl or heterocycloalkyl consisting of 3 to 6 ring atoms. The ring may be monocyclic, bicyclic or polycyclic, wherein the bicyclic or polycyclic system includes a spiro ring, a fused ring, a bridged ring, etc. Unless otherwise specified, the ring optionally contains 1, 2, or 3 heteroatoms independently selected from the group consisting of O, S, and N. The 3-6 membered ring includes 3-6 membered ring, 3-5 membered ring, 4-6 membered ring, 4-5 membered ring, 5-6 membered ring, etc. The term "ring" also includes a ring system containing at least one ring, in which each "ring" independently meets the above definition.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$, and $C_5$ alkyl, etc., and may be monovalent (e.g., methyl), divalent (e.g., methylene), or polyvalent (e.g., methenyl). Examples of $C_{1-6}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, and the like.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl, etc., and may be monovalent (e.g., methyl), divalent (e.g., methylene), or polyvalent (e.g., methenyl). Examples of $C_{1-3}$ alkyl include, but are not limited to, methyl (Me), ethyl (Et), propyl (including n-propyl and isopropyl), and the like.

The term "heteroalkyl", by itself or in combination with another term, refers to a stable linear or branched alkyl radical or a combination thereof consisting of a specified number of carbon atoms and at least one heteroatom or heteroatom group. In some embodiments, the heteroatom is selected from the group consisting of B, O, N, and S, wherein nitrogen and sulfur atoms are optionally oxidized and the nitrogen heteroatom is optionally quaternized. In other embodiments, the heteroatom group is selected from the group consisting of —C(=O)O—, —C(=O)—, —C(=S)—, —S(=O), —S(=O)$_2$—, —C(=O)N(H)—, —C(=NH)—, —S(=O)$_2$N(H)—, and —S(=O)N(H)—. In some embodiments, the heteroalkyl is $C_{1-6}$ heteroalkyl. In other embodiments, the heteroalkyl is $C_{1-3}$ heteroalkyl. The heteroatom or heteroatom group can be located at any interior position of heteroalkyl, including the position where the alkyl is linked to the rest part of the molecule. However, the terms "alkoxy", "alkylamino" and "alkylthio" (or thioalkxoy) are commonly used expressions and refer to those alkyl groups linked to the rest part of the molecule via an oxygen atom, an amino, or a sulfur atom, respectively. Examples of heteroalkyl include, but are not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$, —S(=O)—CH$_3$, and —CH$_2$—CH$_2$—S(=O)$_2$—CH$_3$. At most two heteroatoms can be consecutive, such as, —CH$_2$—NH—OCH$_3$.

Unless otherwise specified, "$C_{3-6}$ cycloalkyl" refers to a saturated cyclic hydrocarbon group consisting of 3 to 6 carbon atoms, including monocyclic and bicyclic ring systems. The $C_{3-6}$ cycloalkyl includes $C_{3-5}$ cycloalkyl, $C_{4-5}$ cycloalkyl, $C_{5-6}$ cycloalkyl and the like, and may be monovalent, divalent or polyvalent. Examples of $C_{3-6}$ cycloalkyl include, but are not limited to, cyclopropyl, cyclobutyl, cyclopentyl, cyclohexyl, and the like.

Unless otherwise specified, the term "3-6 membered heterocycloalkyl", by itself or in combination with other terms, refers to a saturated cyclic group consisting of 3 to 6 ring atoms, of which 1, 2, 3, or 4 ring atoms are heteroatoms independently selected from the group consisting of O, S and N, with the remaining being carbon atoms. The nitrogen atom is optionally quaternized, and the nitrogen and sulfur heteroatoms can be optionally oxidized (i.e., NO and S(O)$_p$, where p is 1 or 2). This includes monocyclic and bicyclic systems, wherein the bicyclic system includes spirocyclic, fused, and bridged rings. Furthermore, with respect to the "3-6 membered heterocycloalkyl", a heteroatom may occupy the position where the heterocycloalkyl is connected to the rest of the molecule. The 3-6 membered heterocycloalkyl includes 4-6 membered, 5-6 membered, 4 membered, 5 membered, 6 membered heterocycloalkyl, and the like. Examples of 3-6 membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl, etc.

Unless otherwise specified, the terms "5-6 membered heteroaromatic ring" and "5-6 membered heteroaryl" can be used interchangeably herein. The term "5-6 membered heteroaryl" refers to a monocyclic group which consists of 5 to 6 ring atoms and has a conjugated pi-electron system, of which 1, 2, 3 or 4 ring atoms are heteroatoms independently selected from the group consisting of O, S and N, the others being carbon atoms. The nitrogen atom is optionally quaternized and the nitrogen and sulfur heteroatoms are optionally oxidized (i.e., NO and $S(O)_p$, where p is 1 or 2). The 5-6 membered heteroaryl can be connected to the rest of the molecule via a heteroatom or a carbon atom. The 5-6 membered heteroaryl includes 5-membered and 6-membered heteroaryl. Examples of the 5-6 membered heteroaryl include, but are not limited to, pyrrolyl (including N-pyrrolyl, 2-pyrrolyl, 3-pyrrolyl, etc.), pyrazolyl (including 2-pyrazolyl, 3-pyrazolyl, etc.), imidazolyl (including N-imidazolyl, 2-imidazolyl, 4-imidazolyl, 5-imidazolyl, etc.), oxazolyl (including 2-oxazolyl, 4-oxazolyl, 5-oxazolyl, etc.), triazolyl (including 1H-1,2,3-triazolyl, 2H-1,2,3-triazolyl, 1H-1,2,4-triazolyl, 4H-1,2,4-triazolyl, etc.), tetrazolyl, isoxazolyl (3-isoxazolyl, 4-isoxazolyl, 5-isoxazolyl, etc.), thiazolyl (including 2-thiazolyl, 4-thiazolyl, 5-thiazolyl, etc.), furanyl (including 2-furanyl, 3-furanyl, etc.), thienyl (including 2-thienyl, 3-thienyl, etc.), pyridinyl (including 2-pyridinyl, 3-pyridinyl, 4-pyridinyl, etc.), pyrazinyl, or pyrimidinyl (including 2-pyrimidinyl, 4-pyrimidinyl, etc.).

Unless otherwise specified, $C_{n-n+m}$ or $C_n$-$C_{n+m}$ includes any one of the specific cases of n to n+m carbons; for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$; $C_{n-n+m}$ or $C_n$-$C_{n+m}$ also includes any range in n to n+m; for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$, etc. Similarly, n–n+m membered represents the number of atoms on the ring is n to n+m; for example, 3-12 membered ring includes 3 membered ring, 4 membered ring, 5 membered ring, 6 membered ring, 7 membered ring, 8 membered ring, 9 membered ring, 10 membered ring, 11 membered ring and 12 membered ring; n–n+m membered also represents any range in n to n+m; for example, 3-12 membered ring includes 3-6 membered ring, 3-9 membered ring, 5-6 membered ring, 5-7 membered ring, 6-7 membered ring, 6-8 membered ring, 6-10 membered ring, etc.

The compounds of the present application can be prepared by a variety of synthetic methods well known to those skilled in the art, including the specific embodiments listed below, embodiments formed by combinations thereof with other chemical synthetic methods, and equivalents thereof known to those skilled in the art. Preferred embodiments include, but are not limited to, the examples disclosed herein.

The solvent used in the present application can be commercially available.

Compounds are named according to conventional nomenclature rules in the art or using ChemDraw® software, and supplier's catalog names are given for commercially available compounds.

List of Abbreviations

| | |
|---|---|
| Pd/C | Pd/C catalyst, containing 10 w % palladium |
| DCM | Dichloromethane |
| NH$_3$•H$_2$O | aqueous ammonia, content of 25%-28% |
| THF | Tetrahydrofuran |
| Boc | Tert-butyloxycarbonyl, an amine protecting group |
| Cbz | Benzyloxycarbonyl, an amine protecting group |
| DMF | N,N-dimethylformamide |
| TFA | Trifluoroacetic acid |
| DCM | Dichloromethane |
| PE | Petroleum ether |
| DMSO | Dimethyl sulfoxide |
| EtOH | Ethanol |
| MeOH | Methanol |
| HOAc | Acetic acid |
| HATU | O-(7-azabenzotriazol-1-yl)-N,N,N',N'-tetramethyluronium hexafluorophosphate |
| EDCI | 1-ethyl-(3-dimethylaminopropyl)carbodiimide hydrochloride |
| HOBt | 1-hydroxybenzotriazole |
| Boc$_2$O | Di-tert-butyl dicarbonate |
| CbzCl | Benzyl chloroformate |
| DIPEA | Diisopropylethylamine |
| SiO$_2$ | 100-200 mesh silica gel powder, for column chromatography |
| IPA | Isopropanol |
| psi | Pound force/square inch, unit of pressure |
| SFC | Supercritical fluid chromatography |
| p-HPLC | Preparative high performance liquid chromatography, for the purification of compounds |
| p-TLC | Preparative thin-layer chromatography, for the purification of compounds |

Compounds are named either manually or by ChemDraw® software, and supplier's catalog names are given for commercially available compounds.

The solvents used in the present application are commercially available and do not require further purification. The reaction is generally performed in an anhydrous solvent under nitrogen atmosphere. Proton nuclear magnetic resonance data are recorded on a Bruker Avance III 400 (400

MHz) spectrometer and chemical shifts reported as ppm downfield from tetramethylsilane. Mass spectra are determined on an Agilent 1200 series plus 6110 (&1956A). LC/MS or Shimadzu MS includes a DAD: SPD-M20A (LC) and Shimadzu Micromass 2020 detector. The mass spectrometer is equipped with an electrospray ion source (ESI) operated in either positive or negative mode.

The Shimadzu LC20AB system equipped with a Shimadzu SIL-20A automatic sampler and a Japanese Shimadzu DAD: SPD-M20A detector was used for analysis of high performance liquid chromatography with an Xtimate C18 (3 m filler, 2.1×300 mm) chromatographic column. 0-60AB_6 min method: linear gradient is applied, wherein elution is initiated with 100% A (A is 0.0675% TFA aqueous solution) and terminated with 60% B (B is 0.0625% TFA in MeCN solution) (the whole process is 4.2 min), and then 60% B is used for elution for 1 min. The chromatographic column is further equilibrated for 0.8 min to reach 100:0 and the total operation time is 6 min. 10-80AB_6 min method: linear gradient is applied, wherein elution is initiated with 90% A (A is 0.0675% TFA aqueous solution) and terminated with 80% B (B is 0.0625% TFA in acetonitrile solution) (the whole process is 4.2 min), and then 80% B is used for elution for 1 min. The chromatographic column is further equilibrated for 0.8 min to reach 90:10 and the total operational time is 6 min. The column temperature is 50° C. and the flow rate is 0.8 mL/min. The scanning wavelength of diode array detector is 200-400 nm.

Thin layer chromatographic (TLC) analysis is performed on silica gel GF254 of Sanpont-group. Speckles are detected with UV light generally and in some cases other methods may also be used. In these cases, the thin layer plate is spread with iodine (acquired by adding 1 g of iodine into 10 g of silica gel and mixing the two completely), vanillin (acquired by dissolving about 1 g of vanillin in 100 mL of 10% $H_2SO_4$), ninhydrin (available from Aldrich) or particular developer (acquired by completely mixing 25 g of $(NH_4)_6Mo_7O_{24} \cdot 4H_2O$, 5 g of $(NH_4)_2Ce(IV)(NO_3)_6$, 450 mL of $H_2O$ and 50 mL of concentrated $H_2SO_4$), and the compound is detected. With a method similar to that described in Still, W C.; Kahn, M.; and Mitra, M. *Journal of Organic Chemistry*, 1978, 43, 2923-2925, the flash column chromatography is performed on 40-63 μm (230-400 mesh) silica gel from Silicycle. Common solvents in flash column chromatography or thin layer chromatography comprise dichloromethane/methanol, ethyl acetate/methanol and hexane/ethyl acetate mixture.

Preparative chromatographic analysis is performed on Gilson-281 Prep LC 322 system with Gilson UV/VIS-156 detector, and the chromatographic column is Agella Venusil ASB Prep C18 (5 m filler, 150×21.2 mm), Phenomenex Gemini C18 (5 m filler, 150×30 mm), Boston Symmetrix C18 (5 m filler, 150×30 mm) or Phenomenex Synergi C18 (4 m filler, 150×30 mm). Low gradient acetonitrile/water is used to elute the compound when the flow rate is about 25 mL/min, wherein the water contains 0.05% HCl, 0.25% HCOOH or 0.5% $NH_3 \cdot H_2O$, and the total operational time is 8-15 min.

DETAILED DESCRIPTION

The present application is described in detail below by way of examples. However, this is by no means disadvantageously limiting the scope of the present application. Although the present application has been described in detail herein and specific examples have also been disclosed, it will be apparent to those skilled in the art that various changes and modifications can be made to the specific examples without departing from the spirit and scope of the present application.

Example 1

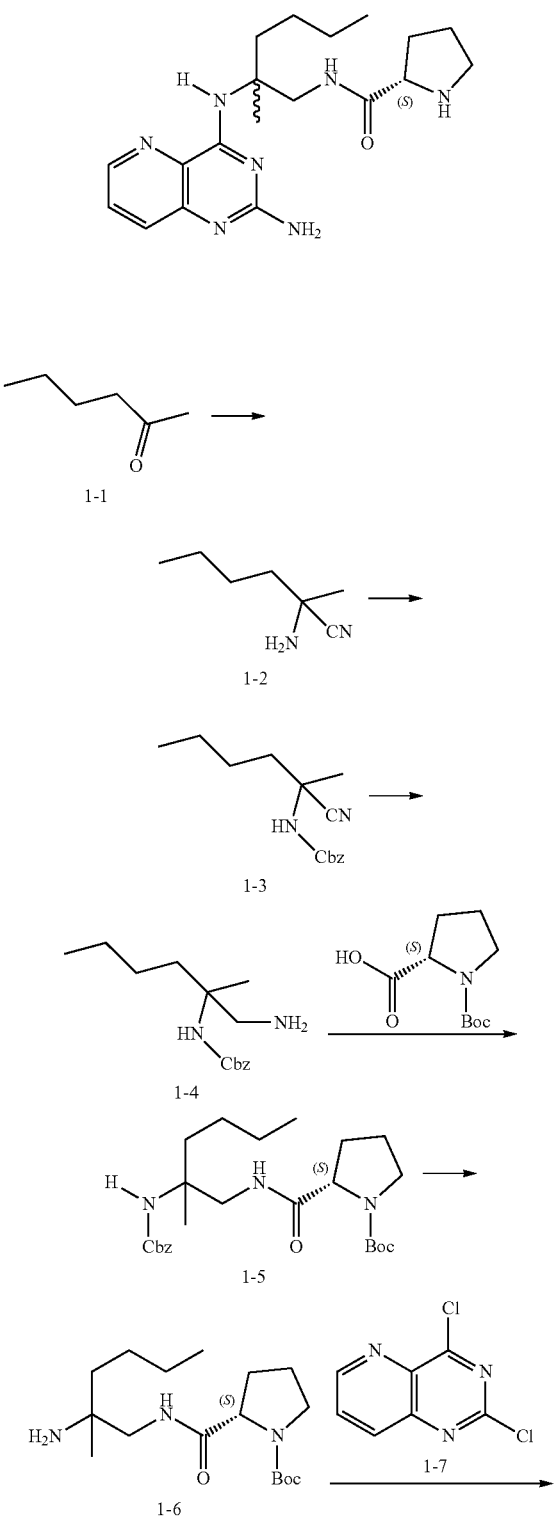

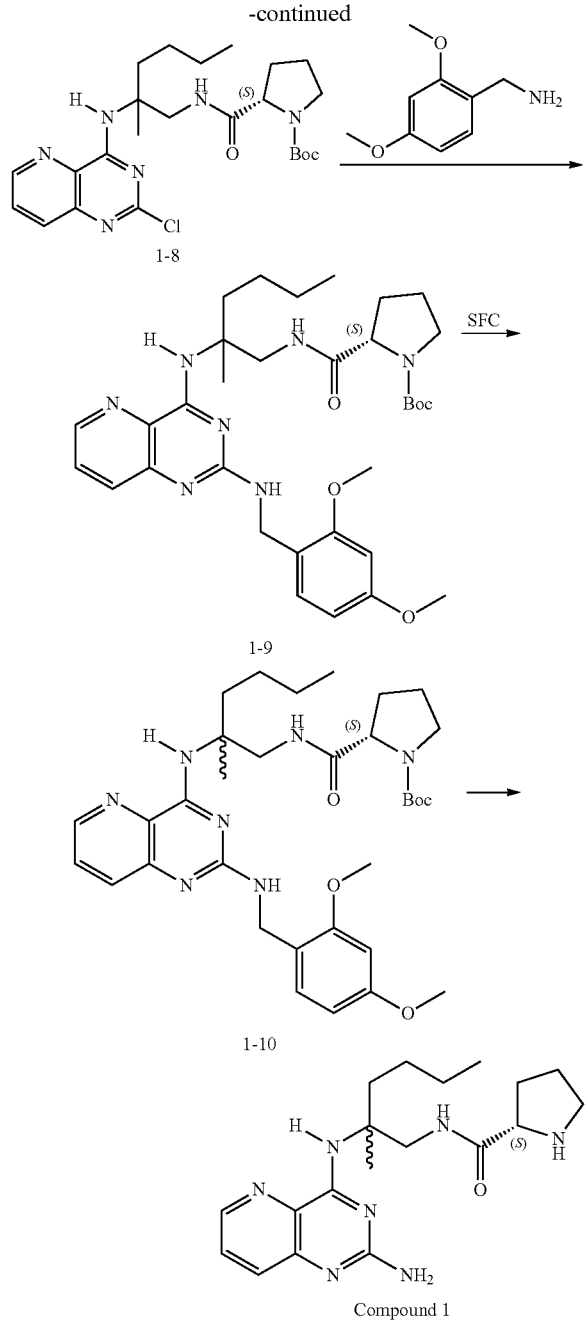

hydrofuran (200.00 mL) and H$_2$O (40.00 mL), and then CbzCl (38.66 g, 226.62 mmol, 32.22 mL) was added dropwise at 0° C. The reaction mixture was stirred at 25° C. for 8 h, and then ethyl acetate (100 mL) and water (50 mL) were added for liquid separation. The organic phase was separated out, washed with brine (100 mL), dried over anhydrous sodium sulfate and concentrated under reduced pressure to remove the solvent, thus giving a crude product. The crude product was purified on a silica gel column (SiO$_2$, PE/EtOAc=1/0-20/1) to give the product 1-3. $^1$H NMR (400 MHz, CDCl$_3$) δ 7.42-7.33 (m, 5H), 5.23-5.11 (m, 2H), 4.93 (br s, 1H), 2.00-1.80 (m, 2H), 1.70 (s, 3H), 1.54-1.35 (m, 4H), 1.00-0.92 (m, 3H). LCMS (ESI) m/z: 261.3 [M+H]$^+$.

Step C: 1-3 (37.00 g, 120.81 mmol) and anhydrous cobalt chloride (31.37 g, 241.62 mmol) were dissolved in methanol (400.00 mL), and sodium borohydride (22.85 g, 604.05 mmol) was added to the reaction mixture in portions at 5-15° C. over 2 h under nitrogen atmosphere. The reaction mixture was stirred at 15° C. for 1 h, and then aqueous ammonia (20%, 500 mL) and ethyl acetate (1000 mL) were added for liquid separation. The aqueous phase was extracted with ethyl acetate (500 mL×2). The combined organic phases were washed with brine (300 mL), dried over anhydrous sodium sulfate and concentrated under reduced pressure to remove the solvent, thus giving the product 1-4. $^1$H NMR (400 MHz, CDCl$_3$): δ 7.31-7.20 (m, 5H), 5.04-4.90 (m, 3H), 2.87-2.57 (m, 2H), 1.67-1.41 (m, 2H), 1.31-1.08 (m, 7H), 0.82 (t, J=7.0 Hz, 3H). LCMS (ESI) m/z: 265.2 [M+H]$^+$.

Step D: Boc-L-proline (894.99 mg, 4.16 mmol) and HATU (1.73 g, 4.54 mmol) were dissolved in acetonitrile (10 mL), and then DIPEA (977.77 mg, 7.56 mmol) was added. Then 1-4 (1 g, 3.78 mmol) was added to the mixture. The reaction mixture was stirred at 15° C. for 0.5 h, and then water (30 mL) and dichloromethane (50 mL) were added for liquid separation. The organic phase was washed with brine (50 mL), dried over anhydrous sodium sulfate and concentrated under reduced pressure to remove the solvent, thus giving a crude product. The crude product was purified on a silica gel column (SiO$_2$, PE/EtOAc=20/1-1/1) to give 1-5.

Step E: 1-5 (1.7 g, 3.68 mmol) was dissolved in methanol (50 mL) and Pd/C (303.57 mg) was added under nitrogen atmosphere. The reaction mixture was purged with hydrogen 3 times, and then stirred at 25° C. for 12 h under hydrogen atmosphere (15 psi). The reaction mixture was filtered and concentrated under reduced pressure to remove the solvent, thus giving 1-6.

Step F: To a mixture of compound 1-6 (900 mg, 2.75 mmol) and compound 1-7 (3.5 g, 5.25 mmol) in tetrahydrofuran (10 mL) was added DIPEA (1.07 mg, 8.25 mmol). The reaction mixture was heated to 70° C. and stirred for 12 h. The reaction mixture was then concentrated under reduced pressure to give crude 1-8. LCMS (ESI) m/z: 491.3 [M+H]$^+$.

Step G: 1-8 (357 mg, 727.05 µmol) and 2,4 dimethoxybenzylamine (729.40 mg, 4.36 mmol) were dissolved in anhydrous dioxane (8 mL), and then DIPEA (281.90 mg, 2.18 mmol) was added. The reaction mixture was warmed to 120° C. and stirred for 12 h under nitrogen atmosphere. After removal of solvent by concentration under reduced pressure, the reaction mixture was dissolved in ethyl acetate (30 mL) and then adjusted to pH 6-7 with 0.5N diluted hydrochloric acid. The resulting reaction mixture was extracted with ethyl acetate (20 mL×3), and the organic phases were combined, washed with saturated brine (50 mL), dried over anhydrous sodium sulfate, filtered and concentrated to give the product 1-9. LCMS (ESI) m/z: 622.6 [M+H]$^+$.

Step H: 1-9 (580 mg, 932.82 µmol) was resolved by SFC (separation column: DAICEL CHIRALPAK AD (250×30

Step A: NH$_3$·H$_2$O (111.16 g, 539.14 mmol, 122.15 mL) and sodium cyanide (9.58 g, 195.47 mmol) were dissolved in water (28.00 mL), and then the reaction mixture was cooled to 15° C. in ice bath, followed by dropwise addition of acetic acid (12.23 g, 203.67 mmol, 11.65 mL). After addition was complete, 1-1 (20.00 g, 199.68 mmol, 24.69 mL) was then added dropwise at 15° C. The reaction mixture was stirred at 35° C. for 12 h and then extracted with DCM (150 mL×3). The combined organic phases were washed with brine (100 mL), dried over anhydrous sodium sulfate and concentrated under reduced pressure to remove the solvent, thus giving the product 1-2. $^1$H NMR (400 MHz, CDCl$_3$) δ 1.69-1.64 (m, 2H), 1.56-1.45 (m, 5H), 1.44-1.36 (m, 2H), 0.96 (t, J=7.2 Hz, 3H).

Step B: 1-2 (22.00 g, 174.33 mmol) and potassium carbonate (72.28 g, 522.98 mmol) were dissolved in tetramm, particle size: 10 μm); mobile phase: [0.1% NH₃·H₂O, IPA] 40%-40%, 3.5 min) to give 1-10 (retention time=2.276 min, ee value: 100%). LCMS (ESI) m/z: 622.4 [M+H]⁺.

Step I: 1-10 (220 mg, 353.83 μmol) was dissolved in TFA (5 mL) and the reaction mixture was stirred at room temperature for 30 min. Then the reaction mixture was concentrated under reduced pressure to give a crude product, which was purified by p-HPLC to give the compound 1. ¹H NMR (400 MHz, CD₃OD) δ 8.64 (dd, J=1.2, 4.4 Hz, 1H), 8.59 (br t, J=6.1 Hz, 1H), 7.89 (dd, J=1.2, 8.4 Hz, 1H), 7.80 (dd, J=4.4, 8.4 Hz, 1H), 4.36-4.25 (m, 1H), 4.06-3.93 (m, 1H), 3.92-3.81 (m, 1H), 3.42-3.32 (m, 2H), 2.52-2.36 (m, 1H), 2.33-2.19 (m, 1H), 2.12-1.90 (m, 3H), 1.87-1.75 (m, 1H), 1.55 (s, 3H), 1.47-1.27 (m, 4H), 0.93 (t, J=7.0 Hz, 3H). LCMS (ESI) m/z: 372.3 [M+H]⁺.

Example 2

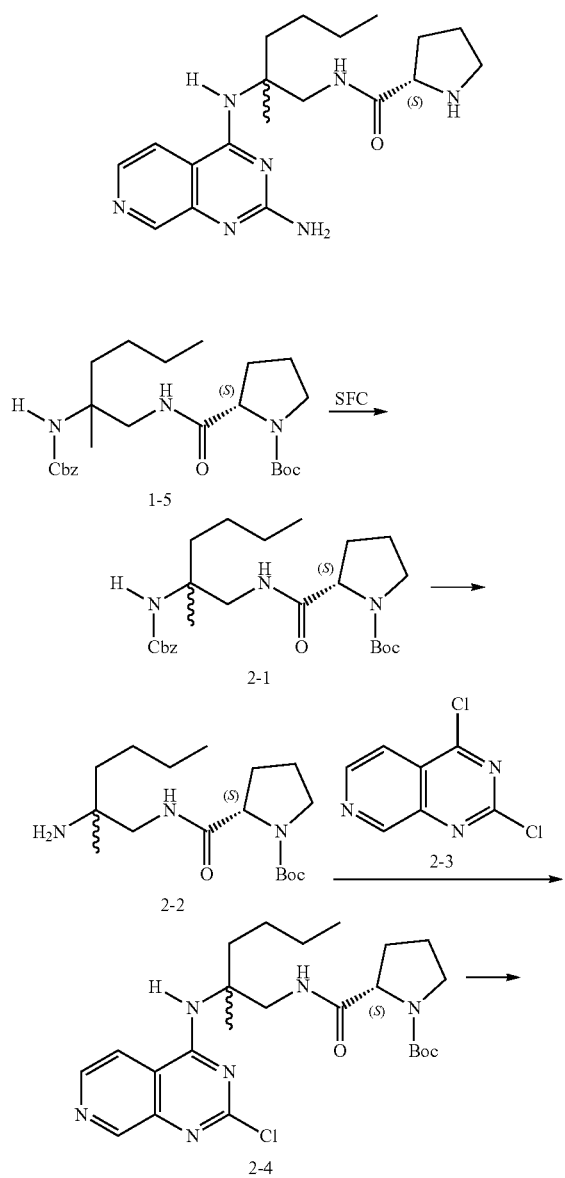

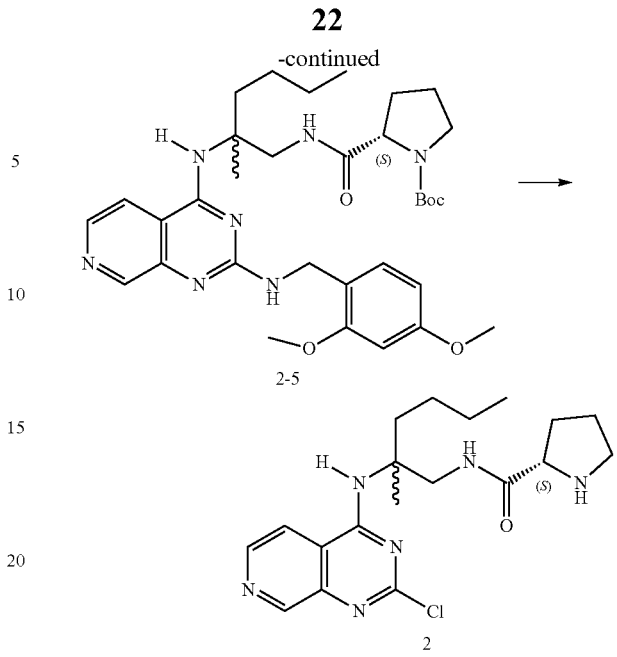

Step A: 1-5 (2 g, 4.33 mmol) was resolved by SFC (separation column: DAICEL CHIRALPAK AD-H (250×30 mm, particle size: 5 μm); mobile phase [0.1% NH₃·H₂O, EtOH] 25%-25%, 1.8 min) to give a single configuration 2-1 (retention time=1.283 min, ee value: 100%).

Step B: 2-1 (600 mg, 1.30 mmol) was dissolved in methanol (20 mL), and then Pd/C (60 mg) was added under nitrogen atmosphere. The reaction mixture was purged with hydrogen several times, and then stirred at 25° C. for 12 h under hydrogen atmosphere (15 psi). The reaction mixture was filtered and concentrated under reduced pressure to remove the solvent, thus giving 2-2. ¹H NMR (400 MHz, DMSO-d6) δ=7.73 (br d, J=4.8 Hz, 1H), 4.17 (dd, J=2.9, 8.3 Hz, 1H), 3.42 (br d, J=4.0 Hz, 1H), 3.35-3.31 (m, 1H), 3.14-3.10 (m, 1H), 2.98-2.88 (m, 1H), 2.20-2.04 (m, 1H), 1.92-1.73 (m, 3H), 1.48-1.36 (m, 9H), 1.28 (br s, 6H), 0.98-0.86 (m, 6H).

Step C: To a mixture of compound 2-2 (83 mg, 253.47 μmol) and compound 2-3 (50.70 mg, 253.47 μmol) in THF (4 mL) was added DIPEA (65.52 mg, 506.93 μmol). The reaction mixture was heated to 70° C. and stirred for 12 h. The reaction mixture was then concentrated under reduced pressure to give crude 2-4. LCMS (ESI) m/z: 492.1 [M+H]⁺.

Step D: 2-4 (124 mg, 252.53 μmol) and 2,4-dimethoxybenzylamine (168.90 mg, 1.01 mmol) were dissolved in anhydrous dioxane (5 mL), and then DIPEA (65.27 mg, 505.07 μmol) was added. The reaction mixture was warmed to 120° C. and stirred for 14 h under nitrogen atmosphere. The reaction mixture was poured into water (10 mL) and extracted with ethyl acetate (10 mL×2). The organic phases were combined, washed with saturated brine (10 mL), dried over anhydrous sodium sulfate, filtered and concentrated. The residue was purified by p-TLC to give compound 2-5. LCMS (ESI) m/z: 622.7 [M+H]⁺.

Step E: 2-5 (60 mg, 96.50 μmol) was dissolved in TFA (2 mL), and the reaction mixture was stirred at room temperature for 14 h. Then the reaction mixture was concentrated under reduced pressure to give a crude product, which was purified by p-HPLC to give compound 2.

¹H NMR (400 MHz, CD₃OD) δ 8.95 (br s, 1H), 8.85 (br t, J=6.1 Hz, 1H), 8.67 (br d, J=4.8 Hz, 1H), 8.44 (d, J=5.5 Hz, 1H), 4.38 (br d, J=7.1 Hz, 1H), 4.14-4.02 (m, 1H), 3.67-3.56 (m, 1H), 3.46-3.32 (m, 2H), 2.57-2.42 (m, 1H), 2.37-2.24 (m, 1H), 2.15-1.89 (m, 4H), 1.58 (s, 3H), 1.44-1.27 (m, 4H), 0.96-0.86 (m, 3H). LCMS (ESI) m/z: 372.1 [M+H]$^+$.
Example 3
Example 3 can be prepared according to the preparation method of Example 2. In step C of Example 2, 2-3 was substituted with 2,4-dichloroquinazoline.
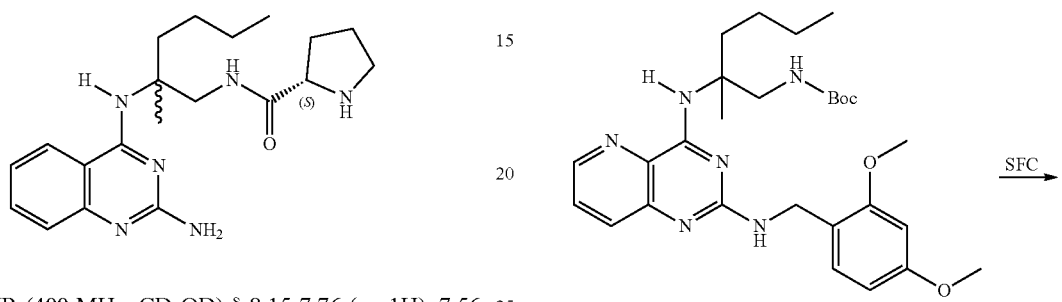
$^1$H NMR (400 MHz, CD$_3$OD) δ 8.15-7.76 (m, 1H), 7.56 (br d, J=1.2 Hz, 1H), 7.30 (d, J=8.3 Hz, 1H), 7.23-7.04 (m, 1H), 3.93 (d, J=13.9 Hz, 1H), 3.82-3.64 (m, 1H), 3.42 (d, J=13.9 Hz, 1H), 3.01-2.86 (m, 2H), 2.26-1.66 (m, 6H), 1.52 (s, 3H), 1.33 (br s, 4H), 0.91 (s, 3H). LCMS (ESI) m/z: 371.1 [M+H]$^+$.
Example 4
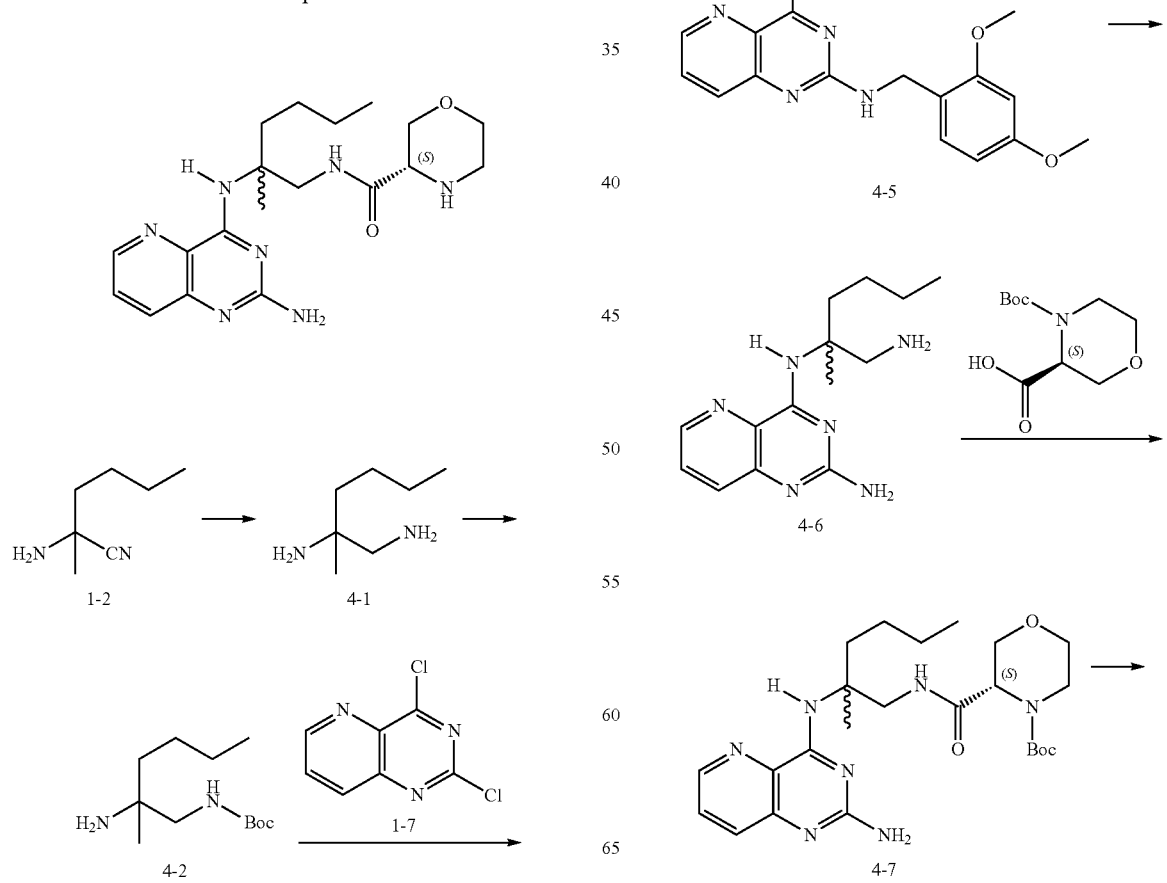
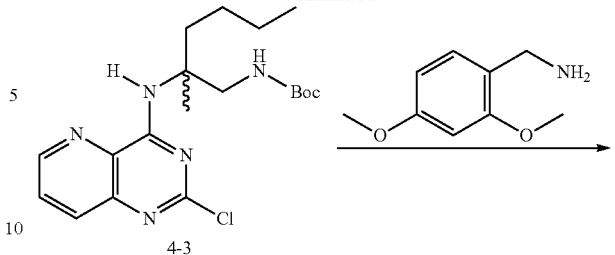

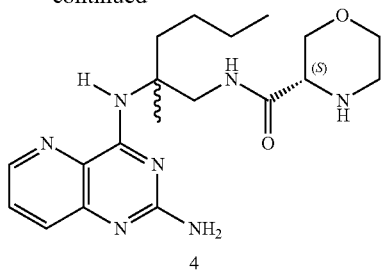

4

Step A: To a solution of 1-2 (50 g, 396.20 mmol) in methanol (300 mL) was added a solution of hydrochloric acid in methanol (4 mol/L, 198.10 mL) and platinum dioxide (1 g, 4.40 mmol) under nitrogen atmosphere. The reaction mixture was purged with hydrogen several times, and then stirred at 25° C. for 32 h under hydrogen atmosphere (50 psi). The reaction mixture was filtered through diatomite and washed with methanol (200 mL), and the filtrate was concentrated under reduced pressure at 45° C. to give compound 4-1.

$^1$H NMR (400 MHz, D20-d$_6$) δ 3.30-3.22 (m, 2H), 1.70 (m, 2H), 1.41 (s, 3H), 1.31-1.23 (m, 4H), 0.851 (m, 3H) Step B: 4-1 (6 g, 29.53 mmol) was dissolved in water (30 mL), and then sodium bicarbonate (6.20 g, 73.84 mmol) was added. Then a solution of (Boc)$_2$O (5.37 g, 24.61 mmol) in methanol (20 mL) was added dropwise at 0-5° C. The reaction mixture was stirred at 0-5° C. for 2 h and then stirred at 25° C. for 12 h. The reaction mixture was added with water (30 mL) and ethyl acetate (50 mL) for liquid separation, and the aqueous phase was extracted with ethyl acetate/isopropanol (3:1) (50 mL×2). The combined organic phases were washed with saturated brine (30 mL), dried over anhydrous sodium sulfate, filtered and concentrated to give a crude product. The crude product was purified on a silica gel column (SiO$_2$, PE/EtOAc=1/1-0/1) to give 4-2.

$^1$H NMR (400 MHz, DMSO-d$_6$) δ 6.70 (br t, J=5.7 Hz, 1H), 2.87 (d, J=6.1 Hz, 2H), 1.39 (s, 9H), 1.30-1.18 (m, 6H), 0.91 (s, 3H), 0.89-0.83 (m, 3H)

Step C: To a solution of 4-2 (2.2 g, 9.55 mmol) and DIPEA (4.4 g, 34.05 mmol) in THF (40 mL) was added 1-7 (13.89 g, 69.44 mmol), and then the reaction mixture was warmed to 70° C. and stirred for 12 h. The reaction mixture was then added with water (50 mL) and ethyl acetate (100 mL) for liquid separation. The organic phase was separated out, washed with saturated brine (30 mL), dried over anhydrous sodium sulfate, filtered and concentrated to give a crude product. The crude product was purified on a silica gel column (SiO$_2$, PE/EtOAc=10/1-0/1) to give 4-3.

LCMS (ESI) m/z: 394.1 [M+H]$^+$

Step D: 4-3 (1.23 g, 3.11 mmol), 2,4-dimethoxybenzylamine (2.53 g, 15.13 mmol) and DIPEA (1.12 g, 9.34 mmol) were dissolved in dioxane (15 mL), and then the reaction mixture was purged with nitrogen 3 times and then stirred at 100° C. for 12 h under nitrogen atmosphere. The reaction mixture was concentrated under reduced pressure to remove the solvent, and the residue was added with ethyl acetate (20 mL) and washed with diluted hydrochloric acid (1 mol/l, 20 mL×2). The organic phase was washed with saturated brine (20 mL×1), dried over anhydrous sodium sulfate, filtered and concentrated. The residue (0.95 g) was resolved by SFC (separation column: DAICEL CHIRALCEL OD (250×30 mm, particle size: 10 μm); mobile phase [0.1% NH$_3$·H$_2$O, IPA] 35%-35%, 4.1 min) to give a single configuration 4-5 (retention time=1.681 min, ee value: 99%).

Step E: 4-5 (420 mg, 353.83 μmol) was dissolved in TFA (2 mL) and the reaction mixture was stirred at 28° C. for 30 min. Then the reaction mixture was concentrated under reduced pressure to give a crude product, which was purified by p-HPLC to give compound 4-6.

Step F: 4-6 was dissolved in dichloromethane (4 mL), and the mixture was cooled to 10° C. in an ice bath. EDCI (40.06 mg, 208.99 μmol), HOBt (28.24 mg, 208.99 μmol) and DIPEA (102.99 mg, 796.16 μmol, 138.68 mL) were then added. After being stirred at 10° C. for 0.5 h, the reaction mixture was cooled to −10° C. and then added with (S)—N-Boc-morpholine-2-carboxylic acid (100 mg, 199.04 μmol). The reaction mixture was stirred at −10° C. for 1 h. The reaction mixture was poured into water (20 mL) and extracted with dichloromethane (15 mL×2). The combined organic phases were washed with water (20 mL), dried over anhydrous sodium sulfate and concentrated under reduced pressure to remove the solvent, thus giving a crude product. The crude product was purified by p-TLC (EA:MeOH=20/1) to give compound 4-7.

LCMS (ESI) m/z: 488.5[M+H]$^+$.

Step G: Compound 4-7 was dissolved in a mixed solvent of trifluoroacetic acid (1 mL) and dichloromethane (1 mL), and the reaction mixture was stirred at 20-25° C. for 0.5 h. The reaction mixture was concentrated under reduced pressure to remove the solvent, thus giving a crude product. The crude product was purified by p-HPLC to give compound 4.

$^1$H NMR (400 MHz, CD$_3$OD) δ 8.39 (dd, J=1.5, 4.3 Hz, 1H), 7.71-7.61 (m, 1H), 7.56 (dd, J=4.2, 8.5 Hz, 1H), 3.98-3.44 (m, 7H), 3.00-2.81 (m, 2H), 2.22-2.07 (m, 1H), 1.83-1.66 (m, 1H), 1.55-1.30 (m, 7H), 0.93 (t, J=7.1 Hz, 3H)). LCMS (ESI) m/z: 388.1[M+H]$^+$

Examples 5, 6 and 7 can be prepared according to the preparation method of Example 4. In step F of Example 4, (S)—N-Boc-morpholine-2-carboxylic acid was substituted with another Boc-protected amino acid.

Example 5

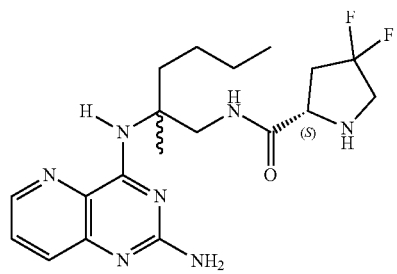

$^1$H NMR (400 MHz, CD$_3$OD) δ 8.38 (dd, J=1.5, 4.3 Hz, 1H), 7.70-7.61 (m, 1H), 7.56 (dd, J=4.2, 8.5 Hz, 1H), 4.02-3.88 (m, 2H), 3.69-3.57 (m, 1H), 3.29-3.04 (m, 1H), 3.09 (ddd, J=10.8, 12.6, 16.0 Hz, 1H), 2.67-2.50 (m, 1H), 2.36 (dq, J=6.2, 14.5 Hz, 1H), 2.18-2.05 (m, 1H), 1.86-1.65 (m, 1H), 1.51-1.27 (m, 7H), 1.20 (t, J=7.1 Hz, 1H), 0.98-0.84 (m, 3H). LCMS (ESI) in/z: 408.1 [M+H]$^+$

Example 6

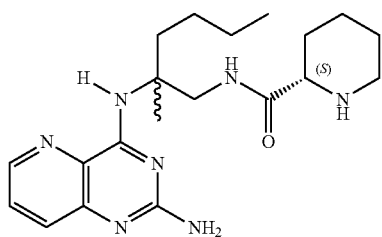

$^1$H NMR (400 MHz, CD$_3$OD) δ 8.37 (dd, J=1.5, 4.3 Hz, 1H), 7.76-7.62 (m, 1H), 7.55 (dd, J=4.2, 8.5 Hz, 1H), 3.86-3.61 (m, 2H), 3.26 (dd, J=2.9, 10.2 Hz, 1H), 3.06 (br d, J=11.9 Hz, 1H), 2.72-2.58 (m, 1H), 2.20-2.07 (m, 1H), 1.95-1.56 (m, 4H), 1.55-1.29 (m, 10H), 0.99-0.88 (m, 3H). LCMS (ESI) m/z: 386.1 [M+H]$^+$

Example 7

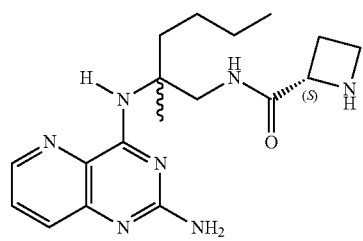

$^1$H NMR (400 MHz, CD$_3$OD) δ 8.38 (dd, J=1.5, 4.3 Hz, 1H), 7.69-7.62 (m, 1H), 7.56 (dd, J=4.2, 8.5 Hz, 1H), 4.37 (t, J=8.4 Hz, 1H), 3.88 (d, J=14.1 Hz, 1H), 3.77-3.58 (m, 2H), 2.65 (m, J=4.3, 8.9, 11.2 Hz, 1H), 2.38-2.10 (m, 2H), 1.84-1.71 (m, 1H), 1.53-1.28 (m, 8H), 0.94 (t, J=7.0 Hz, 3H). LCMS (ESI) m/z: 358.1 [M+H]$^+$

Experimental Example 1: Screening for In Vitro Receptor Binding Activity of Human Toll-Like Receptor 7 (TLR7) and Human Toll-Like Receptor 8 (TLR8)

The HEK-Blue™ hTLR7 (catalog No.: hkb-ht1r7) and HEK-Blue™ hTLR8 (catalog No.: hkb-ht1r8) cell lines used in this experiment were purchased from InvivoGen. The two cell lines were constructed by a human embryonic kidney 293 cell line stably co-transfecting hTLR7 or hTLR8 and inducing expression of Secreted Alkaline Phosphatase (SEAP) reporter gene, wherein SEAP reporter gene was regulated by an IFN-β promoter. The promoter was fused with NF-κB and AP-1 binding sites. hTLR7 or hTLR8 agonist can activate NF-κB and AP-1 and induce the expression and secretion of SEAP. The agonistic activity of compound for hTLR7 and hTLR8 receptors was identified by measuring the expression level of SEAP using QUANTI-Blue™ reagent.

Experimental Procedures:
1. Compound was diluted in 3-fold gradients (10 concentration points in total) and added to the cell plate in duplicate. 1 μL of DMSO was added to each negative control well.
2. The cells cultured in a T150 flask were taken out from a CO$_2$ incubator, and the cell culture supernatant was discarded. The resulting cells were washed once with Dulbecco's phosphate buffered saline (DPBS). The flask was added with about 10 mL of the culture medium, and tapped to detach the cells. The resulting cell mass was gently pipetted evenly. The cells were counted and the cell suspension was adjusted to 500,000 cells/mL with the culture medium. Then 100 μL of diluted cells were added to each well (50,000 cells/well) of a 96-well plate containing the compound.
3. The compound and cells were incubated in an incubator at 37° C., 5% CO$_2$ for 24 h.
4. Activity assay on the compound: 20 μL of the induced cell supernatant from each well was added to a cell culture plate containing 180 μL of QUANTI-Blue™ reagent, and after incubation at 37° C. for 1 h, the optical density absorbance at 650 nm (OD$_{650}$) was assayed for each well using a multi-functional microplate reader.
5. Activity assay on the cells: luciferase signal (RLU) was detected using a multi-functional microplate reader as per the process described in the instructions of ATPlite 1Step.
6. Data analysis: compound activity: OD$_{650}$ values were analyzed using GraphPad Prism software and the dose-response curves of the compounds were fitted to calculate EC$_{50}$ values (half maximal effect concentration) for the compounds.

Experimental results: the results are shown in Table 1.

TABLE 1

| Test compound | Human TLR8 EC$_{50}$ (μM) | Human TLR7 EC$_{50}$ (μM) |
| --- | --- | --- |
| Compound 1 | 0.002 | >15 |
| Compound 2 | 0.006 | >15 |
| Compound 3 | 0.032 | >15 |
| Compound 4 | 0.014 | >15 |
| Compound 5 | 0.106 | >15 |
| Compound 6 | 0.018 | >15 |
| Compound 7 | 0.015 | >15 |

Conclusion: the examples disclosed herein exhibit desirable TLR8 agonist activity and, in terms of TLR8 and TLR7, have specific selectivity for TLR8.

Experimental Example 2: Experimental Procedure for Peripheral Blood Mononuclear Cell TLR8 is a receptor for the innate immune system to sense exogenous pathogens, and can recognize exogenous viral single-stranded RNA and cause the release of a series of cytokines such as TNF-α, IL-12, IFN-γ to elicit an antiviral immune response; TLR7 is another receptor for the innate immune system to sense exogenous pathogens and, when activated, produces primarily such antiviral cytokines as IFN-α. In this experiment, a potential compound of TLR8 agonist was used to stimulate human peripheral blood mononuclear cells (hPBMCs), and the levels of TNF-α, IL-12p40, IFN-γ and IFN-α above were measured to reflect the activation of the compound on TLR8 receptor and its selectivity for TLR8/TLR7.

Experimental Procedures:
1. Fresh blood of healthy volunteers was collected and anticoagulated with an EDTA-K2 anticoagulation tube (catalog No.: BD-8516542);
2. hPBMC cells in the middle cloud-like layer were separated after Ficoll density gradient centrifugation, and washed twice with RPMI1640 (source: Gibco, catalog No.: 224400-089) containing 10% serum, and the culture medium was resuspended to 10 mL. After the cells were counted with Vi-cell cell counter, the concentration of cell suspension was adjusted to $2\times10^6$/mL;

3. The compound was dissolved in DMSO to 100 mM, and diluted to 50 mM and 2 mM with DMSO, which were served as initial concentrations. Then the solutions were each diluted sequentially in a 3-fold gradient (sample at a previous concentration (5 μL)+DMSO (10 μL)) to obtain 8 gradients. The resulting solutions were respectively subjected to 500-fold dilution with the culture medium to prepare the working solutions of the compound;

4. 100 μL of hPBMC suspension and 100 μL of compound working solution were added to each well of a U-bottom 96-well plate, with the final concentrations being 2000 nM, 666.7 nM, 222.2 nM, 74.1 nM, 24.7 nM, 8.2 nM, 2.7 nM and 0.9 nM respectively, and incubated for 24 h. Then the supernatants were collected and cryopreserved at −20° C. for the detection of cytokines TNF-α, IFN-γ and IL-12p40. The other group of compound samples, with the final concentrations being 50 μM, 16.7 μM, 5.6 μM, 1.9 μM, 0.6 μM, 0.2 μM, 0.1 μM and 0.02 μM respectively, were incubated for 24 h. The supernatants were collected and cryopreserved at −20° C. for the detection of IFN-α cytokines;

5. IL-12p40, TNF-α and IFN-γ in the supernatant were detected by flow cytometric bead array (CBA); IFN-α in the cell supernatant was detected by enzyme-linked immuno sorbent assay (ELISA).

6. Data analysis: compound activity: $EC_{50}$ values (half maximal effect concentration) were analyzed using a GraphPad Prism software and the dose-response curves of the compound were fitted to calculate $EC_{50}$ values for the compound.

Experimental results: the results are shown in Table 2.

TABLE 2

| Test compound | IL-12p40 $EC_{50}$ (μM) | IFN-γ $EC_{50}$ (μM) | TNF-α $EC_{50}$ (μM) | IFN-α $EC_{50}$ (μM) |
|---|---|---|---|---|
| Compound 1 | 0.006 | 0.015 | 0.030 | >50 |

Conclusion: the compounds disclosed herein have desirable induction activity for TLR8 pathway specific cytokines IL-12p40, TNF-α and IFN-γ, and relatively low induction activity for TLR7 pathway specific cytokine IFN-α, showing desirably specific selectivity for TLR8 pathway activation.

The invention claimed is:

1. A compound of formula (I), or a stereoisomer thereof, or a pharmaceutically acceptable salt thereof,

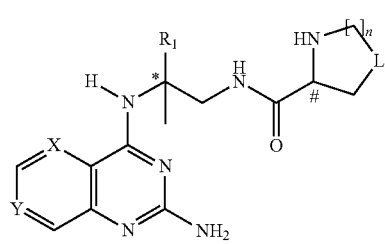

(I)

wherein, the carbon atom with "*" is a chiral carbon atom;

the carbon atom with "#" is a chiral carbon atom present in a form of a single (S) enantiomer or in a form enriched with (S) enantiomer;

X is selected from the group consisting of CH and N;

Y is selected from the group consisting of $CR_2$ and N;

n is selected from the group consisting of 0, 1, 2 and 3;

L is selected from the group consisting of —O— and —$CR_3R_4$—;

$R_1$ is selected from the group consisting of $C_{1-6}$ alkyl, wherein the $C_{1-6}$ alkyl is optionally substituted with 1, 2 or 3 $R_a$;

$R_2$ is selected from the group consisting of H, CN, $NH_2$, halogen, $C_{1-6}$ alkyl, $C_{1-6}$ alkyl-O—, $NHR_b$, $N(R_c)_2$, $C_{3-6}$ cycloalkyl, —C(=O)$R_d$, —C(=O)—O—$R_e$, —O—C(=O)—$R_e$, —S(=O)$_2R_f$ and —S(=O)$R_g$;

$R_3$ and $R_4$ are each independently selected from the group consisting of H, halogen and $C_{1-3}$ alkyl, wherein the $C_{1-3}$ alkyl is optionally substituted with 1, 2 or 3 $R_h$;

alternatively, $R_3$ and $R_4$ are linked to form a 3-6 membered saturated ring, wherein the 3-6 membered saturated ring is optionally substituted with 1, 2 or 3 $R_i$;

$R_a$, $R_b$, $R_c$, $R_d$, $R_e$, $R_f$, $R_g$, $R_h$ and $R_i$ are each independently selected from the group consisting of F, Cl, Br, I, OH, CN, $NH_2$, $C_{1-6}$ alkyl, $C_{1-6}$ heteroalkyl, $C_{3-6}$ cycloalkyl, 3-6 membered heterocycloalkyl, phenyl and 5-6 membered heteroaryl, wherein the $C_{1-6}$ alkyl, $C_{1-6}$ heteroalkyl, $C_{3-6}$ cycloalkyl, 3-6 membered heterocycloalkyl, phenyl and 5-6 membered heteroaryl are optionally substituted with 1, 2 or 3 R;

R is each independently selected from the group consisting of F, Cl, Br, I, OH, CN, $NH_2$, $CH_3$,

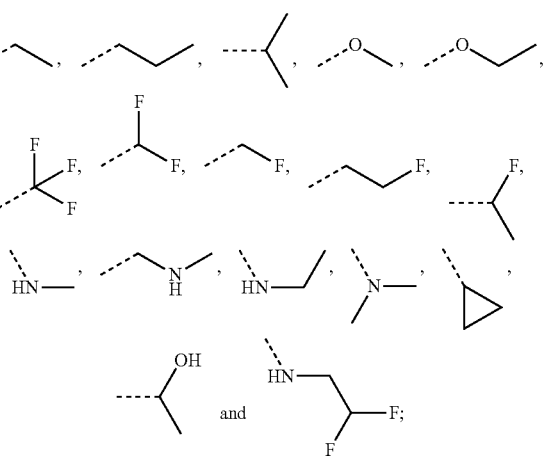

and the $C_{1-6}$ heteroalkyl, 3-6 membered heterocycloalkyl and 5-6 membered heteroaryl each contain 1, 2, 3 or 4 heteroatoms or heteroatom groups independently selected from the group consisting of —NH—, —O—, —S— and N.

2. The compound, or the stereoisomer thereof, or the pharmaceutically acceptable salt thereof according to claim 1, wherein $R_a$, $R_b$, $R_c$, $R_d$, $R_e$, $R_f$, $R_g$, $R_h$ and $R_i$ are each independently selected from the group consisting of F, Cl, Br, I, OH, CN, $NH_2$, $CH_3$,

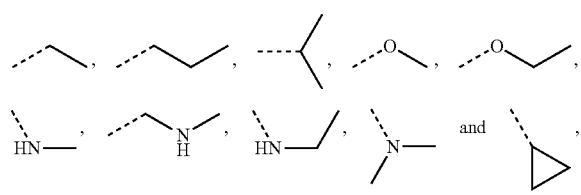

wherein the CH₃,

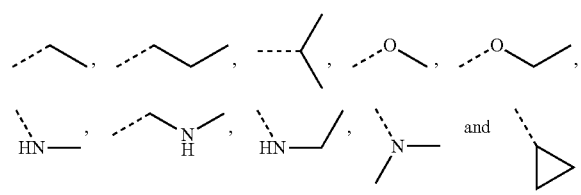

are optionally substituted with 1, 2 or 3 R.

3. The compound, or the stereoisomer thereof, or the pharmaceutically acceptable salt thereof according to claim 2, wherein $R_a$, $R_b$, $R_c$, $R_d$, $R_e$, $R_f$, $R_g$, $R_h$ and $R_i$ are each independently selected from the group consisting of F, Cl, Br, I, OH, CN, NH₂, CH₃,

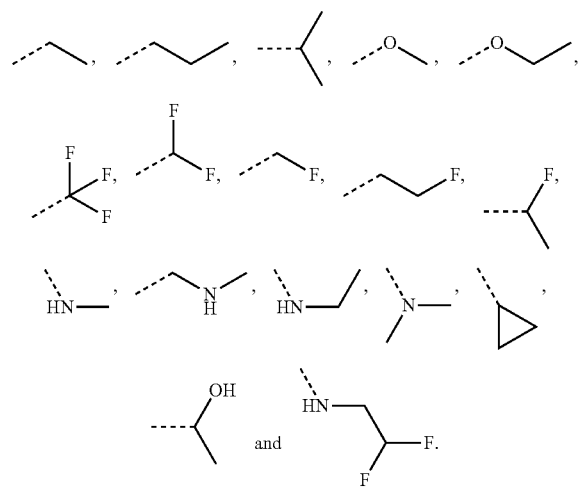

4. The compound, or the stereoisomer thereof, or the pharmaceutically acceptable salt thereof according to claim 1, wherein $R_1$ is selected from the group consisting of

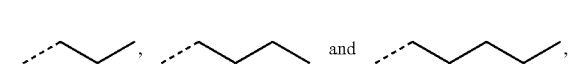

wherein the

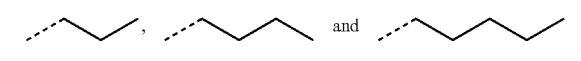

are optionally substituted with 1, 2 or 3 $R_a$.

5. The compound, or the stereoisomer thereof, or the pharmaceutically acceptable salt thereof according to claim 4, wherein $R_1$ is selected from

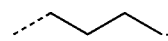

6. The compound, or the stereoisomer thereof, or the pharmaceutically acceptable salt thereof according to claim 1, wherein $R_2$ is selected from the group consisting of H, CN, F, Cl, Br, I, CH₃,

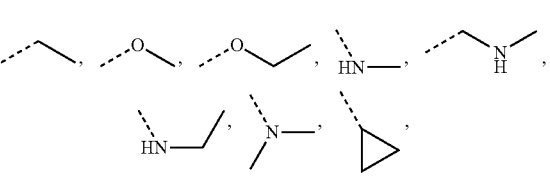

C(=O)CH₃, —C(=O)—O—CH₃, —O—C(=O)—CH₃, —S(=O)₂CH₃ and —S(=O)CH₃.

7. The compound, or the stereoisomer thereof, or the pharmaceutically acceptable salt thereof according to claim 6, wherein $R_2$ is selected from the group consisting of H and F.

8. The compound, or the stereoisomer thereof, or the pharmaceutically acceptable salt thereof according to claim 1, wherein $R_3$ and $R_4$ are each independently selected from the group consisting of H, F, Cl, Br and CH₃, wherein the CH₃ is optionally substituted with 1, 2 or 3 $R_h$.

9. The compound, or the stereoisomer thereof, or the pharmaceutically acceptable salt thereof according to claim 8, wherein $R_3$ and $R_4$ are each independently selected from the group consisting of H and F.

10. The compound, or the stereoisomer thereof, or the pharmaceutically acceptable salt thereof according to claim 1, wherein the structural unit

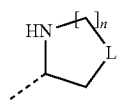

is selected from the group consisting of

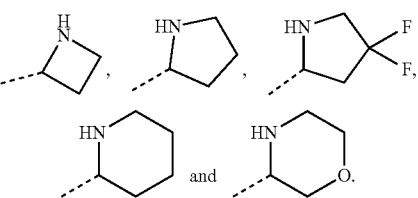

11. The compound, or the stereoisomer thereof, or the pharmaceutically acceptable salt thereof according to claim 1, wherein the compound is selected from compounds represented by the formula below (I-1)
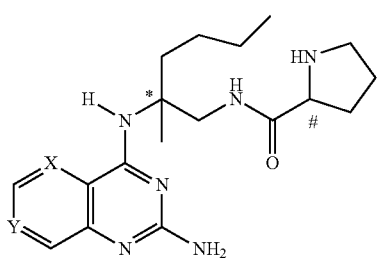
wherein,
"*", "#", X and Y are defined as in claim 1.
12. A compound of a formula selected from the group consisting of the formulas below, or a stereoisomer thereof, or a pharmaceutically acceptable salt thereof:
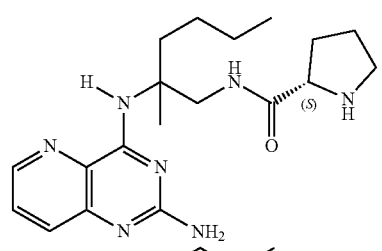
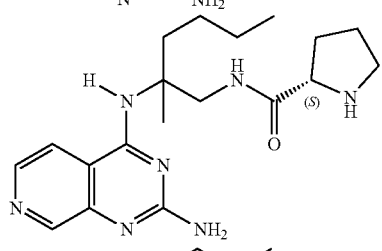
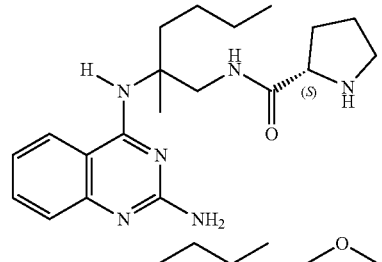
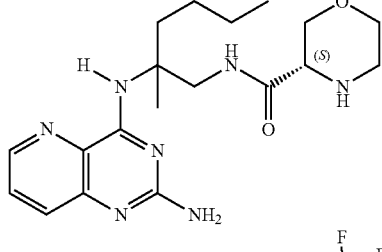
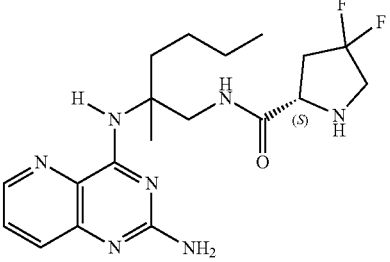
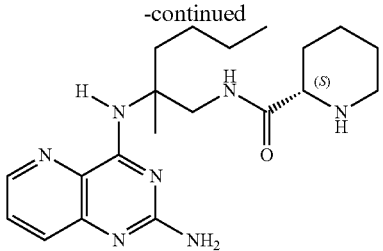
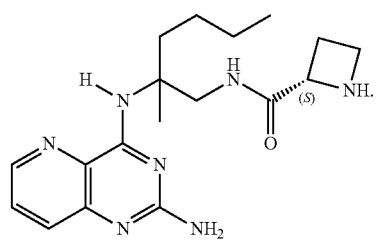
13. A compound of a formula selected from the group consisting of the formulas below, or a stereoisomer thereof, or a pharmaceutically acceptable salt thereof:
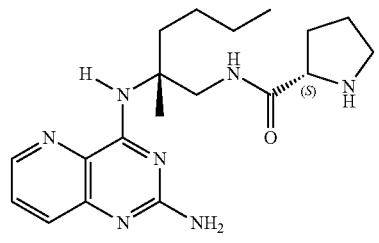
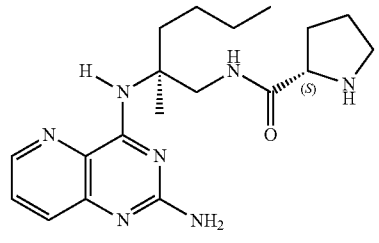
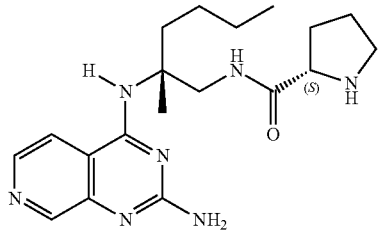
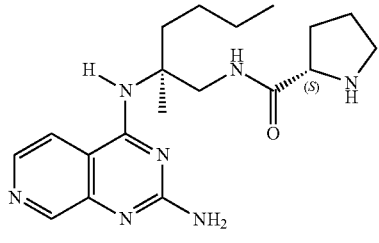

-continued
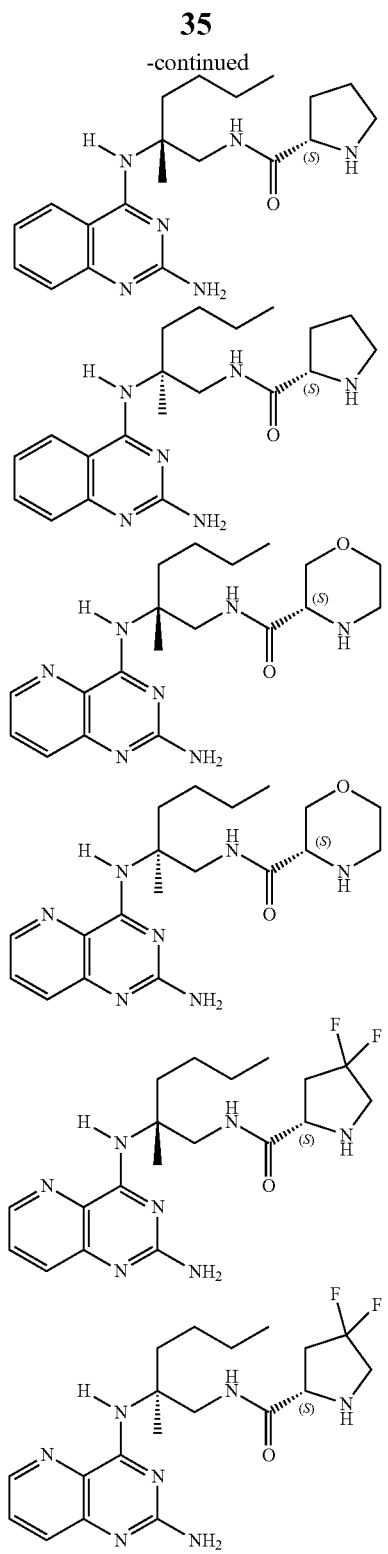
-continued
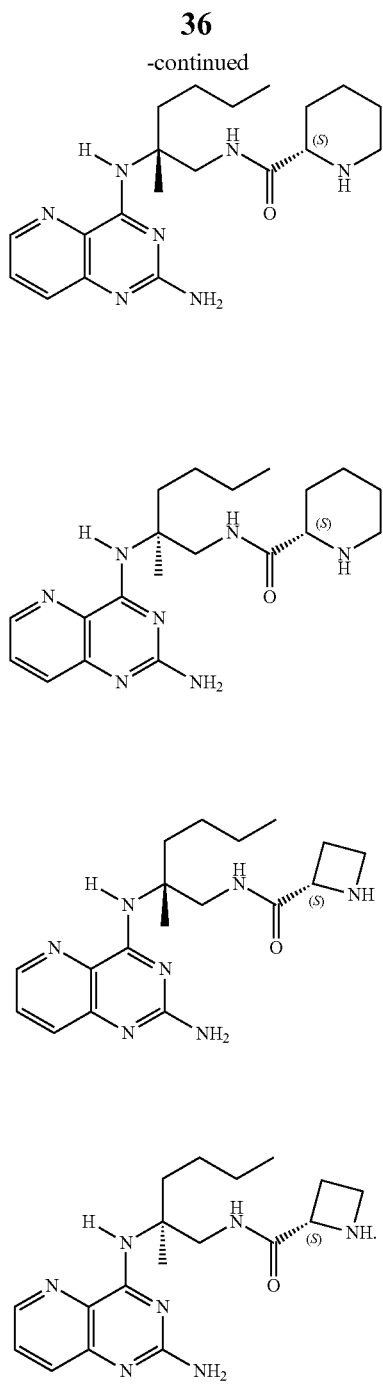
14. A method for treating hepatitis B virus, comprising administering an effective amount of the compound, or the stereoisomer thereof, or the pharmaceutically acceptable salt thereof according to claim 1 to a subject in need thereof.
* * * * *